(12) United States Patent
Bernard et al.

(10) Patent No.: US 6,642,382 B2
(45) Date of Patent: Nov. 4, 2003

(54) METHOD FOR OBTAINING SLIGHTLY COLORED BRANCHED POLYISOCYANATE (S), AND THE RESULTING COMPOSITION

(75) Inventors: Jean-Marie Bernard, Mornant (FR); Frédéric Dallemer, Lyons (FR); Denis Revelant, Genas (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 10/181,495

(22) PCT Filed: Jan. 19, 2001

(86) PCT No.: PCT/FR01/00186
§ 371 (c)(1),
(2), (4) Date: Nov. 12, 2001

(87) PCT Pub. No.: WO01/53277
PCT Pub. Date: Jul. 26, 2001

(65) Prior Publication Data
US 2003/0125554 A1 Jul. 3, 2003

(30) Foreign Application Priority Data
Jan. 20, 2000 (FR) .............................................. 00 00688
May 4, 2000 (FR) .............................................. 00 05736

(51) Int. Cl.[7] .......................................... C07D 251/34
(52) U.S. Cl. ..................................... 544/193; 544/221
(58) Field of Search ................................ 544/193, 221

(56) References Cited

U.S. PATENT DOCUMENTS

| 4,324,879 A | 4/1982 | Bock et al. |
| 5,013,838 A | 5/1991 | Scholl |
| 5,232,998 A | 8/1993 | Buehler et al. |
| 5,489,663 A | 2/1996 | Brandt et al. |
| 5,691,440 A | 11/1997 | Katz et al. |
| 5,705,594 A | 1/1998 | König et al. |
| 5,837,796 A | 11/1998 | Scholl et al. |
| 5,914,383 A | 6/1999 | Richter et al. |
| 6,093,817 A | 7/2000 | Kohlstruk et al. |

FOREIGN PATENT DOCUMENTS

| DE | 4405054 | 8/1995 |
| DE | 19754748 A1 | 6/1999 |
| EP | 0010589 | 5/1980 |
| EP | 0330966 A2 | 9/1989 |
| EP | 0524501 A1 | 1/1993 |
| EP | 0668271 | 8/1995 |
| EP | 0780418 | 6/1997 |
| EP | 0818485 | 1/1998 |
| WO | 99/23128 | 5/1999 |

OTHER PUBLICATIONS

*Chemical Abstracts*, vol. 131, No. 24, Abstract No. 323875, XP–002150287 (abstract of JP 11 302351), published by American Chemical Society, Columbus, Ohio (1999).

*Primary Examiner*—John M. Ford
(74) *Attorney, Agent, or Firm*—Burns, Doane, Swecker & Mathis, L.L.P.

(57) ABSTRACT

The invention concerns a method for cyclotrimerization of isocyanate functions by action of a catalyst based on quaternary ammonium or phosphonium. The invention is characterised in that said isocyanate functions are branched and said onium ions are selected among those whereof the total amount of carbons is not more than 30 and not less than 12; and whereof the counterion is selected among the anions corresponding to weak acids whereof the $pK_A$ is not less than 8, preferably not less than 10, more preferably not less than 12, whereof the substituents are aliphatic compounds and do not have an unsaturation in beta; and said onium ions comprise at least 2 radicals of more than 6, advantageously more than 10, preferably more than 12 carbon atoms.

15 Claims, No Drawings

METHOD FOR OBTAINING SLIGHTLY COLORED BRANCHED POLYISOCYANATE (S), AND THE RESULTING COMPOSITION

The subject of the present invention is a process for preparing polyisocyanates-polyisocyanurates by catalytic cyclotrimerization of polyisocyanate monomers. It relates more particularly to the cyclotrimerization of isocyanate functional groups carried by $sp^3$-hybridized carbons of a particular kind. These carbons are carbons either in the neopentyl position, that is to say said carbon is linked to a tertiary radical such as tert-butyl, or said carbon is a secondary or tertiary carbon, preferably belonging to an aliphatic ring.

The cyclotrimerization of isocyanates has been known for several decades. Such trimerizations generally involve mechanisms which are basic by nature. These bases may be ionic by nature, such as hydroxides or salts of a strong base and strong acid. These bases may also be nonionic bases but may have a very accessible and highly basic electron pair.

The first trimerizations carried out were on aromatic isocyanates, that is to say on isocyanates carried by one of the member carbons of an aromatic ring. Such trimerizations do not pose any particular difficulty and suitable catalysts are readily found for easily carrying out trimerizations of aromatic isocyanates.

The problems inherent with aromatic isocyanates have led to the development of aliphatic isocyanates which have chemical and physical properties which are different and often much improved over aromatic isocyanates.

Most aliphatic isocyanates are too volatile to be used as such. It is therefore necessary to increase their molecular weights by producing either oligomers (biurets, trimers, etc.) or oligo-condensates with polyols.

The trimerization of linear-chain aliphatic isocyanates is now well controlled and there are available catalysts capable of carrying out trimerizations efficiently, that is to say with good yields and developing little coloration.

On the other hand, for reasons which are not fully elucidated, the trimerization of branched aliphatic isocyanates, and especially of cycloaliphatic isocyanates or those in the neopentyl position, remains difficult because, on the one hand, of the difficulty of finding catalysts giving satisfactory yields and satisfactory productivity and because, on the other hand, these derivatives have a strong propensity to develop within them undesirable coloration.

Coloration problems, as mentioned above, have already been treated in the case of linear aliphatic isocyanates such as HDI (hexamethylene diisocyanate), but the techniques used are not easily transposable to branched-type isocyanates, such as isocyanates in neopentyl, cycloaliphatic and tertiary positions, in particular because the reactivity of these branched isocyanates is very significantly less than that of linear isocyanates, with the result that the catalysts used for linear aliphatic isocyanates often give low, or even very low, yields in the case of branched isocyanates.

Thus, it has been proposed to use as basic anion a fluoride anion for carrying out cyclotrimerizations of linear aliphatics without coloration, but this technique cannot easily be used for cycloaliphatics since the yields are very significantly lower in their case.

The degassing of isocyanate monomers has also already been described for the purpose of cyclotrimerizing HDI.

Thus, EP 330 966 discloses a process for trimerizing HDI with the help of a quaternary ammonium hydroxide in which the starting HDI is stripped of carbon dioxide down to a residual content of less than 20 ppm by weight, so as to reduce the amount of catalyst to less than 0.03% by weight for the purpose of reducing the coloration of the final reaction mixture.

EP 524 501 discloses a process for preparing polyisocyanates comprising isocyanurate groups and allophanate groups from HDI by using, as catalyst, a trimethylbenzylammonium hydroxide or a quaternary ammonium hydroxide in which the substituents are $C_1$–$C_{20}$ alkyl groups optionally substituted with hydroxyl groups. It is specified in that document that the starting HDI mixture contains less than 10 ppm $CO_2$.

However, the catalysts illustrated in that document have in three cases methyl substituents, the fourth substituent being either a benzyl group, or a hydroxyalkyl group.

U.S. Pat. No. 5,232,988 discloses a process for preparing blocked polyisocyanates comprising a trimerization reaction on cyclic diisocyanates such as IPDI in the presence of quaternary ammonium carboxylates, phenolates or hydroxides in which the starting diisocyanate is treated by bubbling into it an inert gas.

U.S. Pat. No. 5,914,383 discloses the preparation of a polyisocyanate composition comprising trimers of the iminooxadiazine-dione type and optionally isocyanurate groups in the presence of a polyfluoride as catalyst.

That document discloses in particular the preparation of a composition of the aforementioned type from HDI and IPDI, in which, before the proper catalytic reaction, the gases dissolved in the starting isocyanate mixture are removed.

DE 19 754 748 and EP 927 731 disclose processes for preparing polyisocyanates from IPDI using starting monomers having low chlorine contents, obtained especially by what is referred to as the "urea" process.

On the other hand, EP 379 914 and U.S. Pat. No. 5,013,838 recommend the addition of carbon dioxide during trimerization of aliphatic and/or cycloaliphatic organic diisocyanates, using a catalyst consisting of an ammonium or phosphonium fluoride.

This is why one of the objectives of the present invention is to provide a process which allows branched isocyanate trimers to be obtained while preventing the development of undesirable coloration.

Another object of the present invention is to provide a process which allows good yields and good productivity to be achieved.

Another objective of the present invention is to provide a process which allows the trimerization of cycloaliphatic isocyanates and especially of IPDI (often referred to as isophorone diisocyanate).

Another objective of the present invention is to provide a process which allows the trimerization of cycloaliphatic isocyanates, by improving the reactivity of the catalytic system used for this purpose.

These objectives, and others which will appear later, are achieved by means of a process for trimerizing branched isocyanate functional groups by the action of a quaternary-ammonium- or quaternary-phosphonium-based catalyst, of which the sum of the carbons is at most equal to 30 and at least equal to 12; of which the counterion is chosen from anions corresponding to weak acids whose $pK_A$ is at least equal to 8, preferably 10 and more preferably 12; of which the substituents are aliphatic (that is to say they are linked to the atom carrying the positive charge via an $sp^3$-hybridized carbon atom) and do not possess unsaturation in the beta position (as the benzyl, allyl or propargyl positions have); and in that said oniums comprise at most 2 radicals of more than 6, advantageously more than 10 and preferably more than 12 carbon atoms.

The subject of the invention is also a process for preparing polyisocyanates by cyclotrimerizing isocyanate functional groups carried by isocyanates having a branched hydrocarbon backbone, characterized in that it comprises the following steps:

a) supplying of starting isocyanate monomers;

b) removal of the reactive gases from said isocyanate monomers;

c) optionally, supplying of a starting reaction mixture comprising said starting isocyanate monomers;

d) addition of a cyclotrimerization catalyst consisting of a quaternary ammonium or phosphonium compound, as defined above;

e) reaction until the desired degree of conversion obtained; and f) optionally, removal of the monomers that have not reacted;

the order of steps b) and c) not mattering.

Thus, removal of the reactive gases may take place on the starting isocyanates themselves or after these have been introduced into a possible reaction mixture comprising a suitable solvent.

It goes without saying that when the reaction is carried out with no solvent, directly in the mass of isocyanates, step c) may be omitted.

Advantageously, no substituent of the "onium" (ammonium or phosphonium) compounds carries a hydroxyl functional group (such as a phenol or alcohol).

Furthermore, according to one of the preferred embodiments of the present invention no substituent has fewer than 2, advantageously fewer than 3, carbon atoms.

According to another preferred method of implementation, all of the substituents have at least 1 and at most 2 radicals of more than 12, advantageously more than 10 and preferably more than 6 carbon atoms.

The substituents are advantageously chosen from alkyls, including aralkyls and cycloalkyls. It is preferable that they be not branched in the alpha position or even in the beta position. It is also desirable that they be not functionalized. However, ether functional groups are acceptable, and especially those of the type arising from the opening of the epoxides by an alcohol and an alcoholate.

According to the present invention, are considering as acids not only the usual protic acids but also water and alcohols and any compound that can undergo the extraction of a proton.

The preferred acids are essentially water and alcohols, which means that the counterions of the quaternary ammonium are introduced in the form of hydroxide or alcoholate.

However, it would not be outside the scope of the present invention to manufacture in situ compounds of this type. This is because, during the research which led to the present invention, it was discovered that the structure of the ammonium or phosphonium plays an important role in the development of colorization subsequent to the polymerization reaction.

It turns out in particular that the presence of methyl and of benzylic by nature compounds plays a deleterious role as regards the coloration of the composition after trimerization.

The best results have been obtained when the identical or different radicals substituting the ammonium or phosphonium are chosen from propyl, butyl and pentyl, these radicals preferably being all linear.

The present invention is aimed at the trimerization of polyisocyanate compounds in general and, preferably, those carrying two isocyanate functional groups, said polyisocyanate compounds being denoted in the present description by isocyanate monomers.

However, during the reaction other compounds may be formed depending on the nature and the formulation of the catalyst and, where appropriate, on the cocatalyst, as disclosed in Application WO 99/23128, especially dimers, aminooxidiazine diones, carbamates, allophanates, biurets, etc.

Although the present invention may be aimed at the trimerization of branched monomers with unbranched, that is to say linear, monomers, such as HDI, it is mainly aimed at the trimerization of or the trimerization between different compounds belonging to the same family of branched monomers.

The term "branched monomers", as already mentioned, is understood to mean either a monomer of which at least one isocyanate functional group is in a cycloaliphatic, secondary, tertiary or neopentyl position. These monomers are advantageously cycloaliphatic monomers.

Thus, among these products, those which are preferred are cycloaliphatic. These monomers are advantageously such that at least one, advantageously both, isocyanate functional group(s) is, or are, distant from the closest ring by at most one carbon and preferably linked directly to it. Furthermore, these cycloaliphatic monomers advantageously have at least one, preferably two, isocyanate functional groups chosen from secondary, tertiary or neopentyl isocyanate functional groups.

The best results are obtained when the cycloalipiatic monomer has a low degree of conformational freedom. As monomers capable of giving good results, mention may be made, for example, of the following monomers:

compounds corresponding to the hydrogenation of the aromatic ring or rings carrying the isocyanate functional groups of aromatic isocyanate monomers and especiall y TDI (toluene diiisocyanate) and diisocyanatobiphenyls, the compound known by the abbreviation $H_{12}MDI$, the various BICs [bis(isocyanatomethylcyclohexane)] and cyclohexylene diisocyanates, these being optionally substituted;

and most particularly norbornane dtsocyanate, often denoted by its abbreviation NBDI;

isophorone diisocyanate, or IPDI, or more specifically 3-isocyanatomethyl-3,5,5-trimethyl-cyclohexyl isocyanate.

The starting monomers may also be products from the oligomerization of low-molecular-mass isocyanates, these oligomerization products carrying isocyanate functional groups. In this case, it is unnecessary to separate the unconverted oligomer from the reaction product formed.

The work by the inventors, who are the authors of the present invention, has allowed them to discover that the polymerization of isocyanates of the type described above may be carried out with a high yield, and a substantially reduced coloration, by the combination of a catalyst of the type described below and a step in which the reactive gases dissolved in the reaction mixture, comprising the starting monomers on which the subsequent polymerization reaction is carried out, are removed.

The term "reactive gases" is understood to mean the gases capable of interfering with the catalytic reaction of polymerization, especially trimerization, as opposed to inert gases.

These are especially $CO_2$, but also reactive gases from the air, that is to say the gases other than nitrogen and rare gases, especially oxygen, together with chlorine and possibly chlorinated volatile compounds coming especially from the phosgenation step.

The inventors have also determined that although the sensitivity of the reaction is influenced by the content of $CO_2$ dissolved in the reaction mixture, other gases present, especially air, do have a substantial influence on the way the reaction evolves. Thus, the removal of the reactive gases greatly favors the trimerization reaction, even when the $CO_2$ content of the starting monomers is as low as of the order of 1 to 2 ppm.

The inventors have also found that the content of chlorinated compounds, defined by the content of total chlorine, has only a minimal influence on the sensitivity of the reaction.

The reactive gases may be removed by any means known to those skilled in the art, especially by creating a vacuum, by diffusing in an inert gas or else by the use of molecular sieves or chemical traps, or a combination of one or more of these methods.

When the starting isocyanate monomers have been stored for a long time, generally more than two months, which results in an increase in the dissolved reactive gases, it is generally preferable to remove the dissolved reactive gases by subjecting the reaction mixture to a vacuum followed by the introduction of an inert gas.

The vacuum is generally less than $1 \times 10^4$ Pa (100 mbar).

When the starting monomers have been stored for a shorter time, the introduction by diffusion into the liquid reaction mixture of an inert gas is generally sufficient.

Advantageously, the inert gas is nitrogen or a rare gas, for example argon. The diffusion is carried out at a temperature of around 0 to 70° C. Higher temperatures may be used.

The diffusion may be carried out by sparging. However, the degassing is all the more effective as the size of the gas bubbles generated is small. For this purpose, the diffusion tools will be adapted so that the removal of the reactive gases is rapid, without causing the diffusion devices used to he clogged.

The creation of a vacuum and/or the diffusion are carried out for a time long enough to lower the amount of reactive gases in the starting reaction mixture. In particular, degassing is considered to be proper when the dissolved $CO_2$ is less than 20 ppm, and preferably less than 2 ppm.

The amount of $CO_2$ and the content of gases other than $CO_2$ are advantageously determined by conventional analytical techniques, especially by gas chromatography, using for standards profiles obtained with injections of variable volumes of pure $CO_2$ and/or other pure gases.

The optimum degassing conditions also depend on the conditions under which the isocyanates are treated after they have been synthesized, in general by phosgenation, and on the storage conditions.

In particular, the degassing operation may be carried out after phosgenation of the amines, once the mixture has been purified and has stabilized, under the conditions below. If it is kept under proper conditions (in the dark, at a temperature below 30° C. in airtight and especially moisture-tight containers), the isocyanate monomer may be used in the trimerization process even after a prolonged stored period (two to four months, or longer).

However, to be sure of obtaining low coloration, it is preferable to treat the isocyanates stored for a long period, as described below.

Advantageous conditions for removing the quantities of dissolved reactive gases are, in the case of quantities of starting monomers of around 500 g, after they have been stored for a period of greater than two months, a vacuum of 15 mbar for a long enough time, generally one hour at room temperature, followed by diffusion of an inert gas, for example nitrogen, by sparging or the like into the liquid or the mass for about 30 minutes.

For starting monomers stored for a shorter period of time, simple diffusion of nitrogen, generally by sparging, for a time of 30 minutes at room temperature is sufficient, for the same quantity of starting monomers.

If the gas to be removed is highly acidic, that is to say has a pH value of less than 3 (Handbook, 67$^{th}$ Ed., p D-146 of Chemistry and Physics), it is preferable to carry out the degassing before the introduction of the catalyst, in order to prevent irreversible poisoning of the catalyst.

Conversely, when the gas to be removed is not highly acidic, in particular in the case of $CO_2$, the degassing may be carried before or after the catalyst has been introduced and also during the step of trimerizing the starting isocyanates.

The inventors have also shown that the formulation of the catalyst also has an influence on the reaction kinetics. In particular, in the case of aqueous formulations, water reacts with the isocyanate to give biuret and $CO_2$. The $CO_2$ generated would result in a reduction in the reaction rate. This is why it is preferable to maintain continuous diffusion of inert gas when aqueous catalyst formulations are used.

This also makes it possible to use very small quantities of catalyst and avoids the successive introduction of small quantities of catalyst in order to maintain the reactivity.

Aqueous or hydroalcoholic formulations are preferred, on account of the solubility of oniums in these media before introduction into the reaction mixture, due to the hydrogen dissolved in these solutions.

The operating conditions for step e) of the process according to the present invention may be those which are usually employed for the trimerization of linear aliphatics, in particular the temperature may be chosen between 40 and 100° C., preferably between 50 and 90° C.

A particularly satisfactory operating point lies between 60 and 80° C.

It is also possible to start to heat the reaction mixture before the end of step b) in which the dissolved reactive gases are removed, particularly when said step consists of simply sparging an inert gas.

During the study which led to the present invention, it was shown that other parameters have an influence on the reduction in coloration. The effects of these parameters are favorable by themselves or in combination with the other parameters in the present application, which were mentioned above.

Thus, it has been demonstrated that prior distillation of the starting monomers makes it possible to reduce the coloration developed during the trimerization reaction.

Usually, the trimerization reactions using quaternary oniums are blocked by heating. During the study which led to the present invention, it was shown that this catalyst deactivation technique gives very poor results as regards coloration. It was therefore shown to be preferable to use another technique, known for linear alciphaics, namely the addition of a high-strength acid such as sulfonic acids, for example mesylic, tosylic or phosphoric acids, or a medium-strength acid, preferably an ester of an acid containing phosphorus. As esters of acids containing phosphorus, mention may be made of phosphate esters, especially monoesters and diesters. Mention may also be made of phosphonates, preferably monoesterified ones, and phosphinates.

Poisoning of the catalyst is, however, preferably achieved by means of acid esters of phosphoric acid, and especially dialkyl phosphoric esters, in particular such as dibutyl phosphate and di-2-ethylhexyl phosphate.

The manner of introducing the catalyst according to the invention also plays a role. Thus, when the catalyst is introduced into an aqueous mixture, the coloration develops less than in the case in which the catalyst is introduced into an alcoholic mixture.

However, hydroalcoholic solvents give quite good results.

To prevent regions of reaction runaway, it is desirable to introduce the catalyst in the form of a solution with a proper dilution by mass. Good results are given with 0.5 wt % to 40 wt % catalyst solutions.

The diluants must, on the one hand, ensure the dissolution of the ionic compound formed by the catalyst and, on the other hand, ensure diffusion into the medium formed by the monomers of the reaction mixture. Mixtures of water (0 to 50%, advantageously 5 to 40%), butanol (0 to 50%, preferably 5 to 40%) and heavy (greater than or equal to $C_8$) alcohol(s) or alcohol ethers (2-ethoxy-ethylene glycol) (qsp 100%) give good results.

Although it is preferable to work using relatively dilute catalyst solutions, it is possible, according to the present invention, to use highly concentrated catalyst solutions provided that they are introduced at low temperature, advantageously at room temperature or preferably below room temperature, and provided that homogenization takes place before the process of heating the reaction mixture is initiated.

In general, the trimerization is carried out to the desired degree of conversion. For obvious economic reasons, it is preferred to stop the reaction at degrees of conversion of the isocyanate functional groups of at least 5% and preferably between 10 and 50%. At high degrees, greater than 50%, the polyisocyanates generally have a high viscosity not easily compatible with the subsequent application conditions. Once the polymerization reaction has stopped, the rest of the monomers are generally removed, by evaporation or distillation on a thin film and under a high vacuum.

The amount of catalyst used is advantageously between $10^{-5}$ and $10^{-2}$ times the total mass of the isocyanate monomers introduced, preferably $10^{-4}$ to $10^{-3}$, expressed as amounts by mass of the catalyst without solvent In the case of oligomers, amounts of catalyst such that the ratio of the mass of catalyst to the mass of isocyanate functional groups is between $10^{-5}$ and $10^{-2}$ are preferred.

The present invention is also aimed at compositions comprising:

20 wt % to 80 wt % of compound(s) having isocyanurate rings produced from cycloaliphatic monomer(s);

$10^{-6}$ to $10^{-2}$ of a quaternary ammonium or phosphonium, the sum of the carbons of which is at most equal to 25 and at least equal to 15 and no substituent of which has fewer than 2, advantageously 3, carbon atoms;

20% to 80% of cycloaliphatic monomer (s);

and having a Hazen color value, relative to the percentage by mass of compounds) containing isocyanurate rings, of at most 1 Hazen, advantageously at most 0.75 Hazen and preferably at most 0.50 Hazen.

The following nonlimiting examples illustrate the invention.

The method of quantitatively determining the NCO functional groups is carried out according to the AFNOR NFT 52-132 standard (reaction of isocyanate functional groups with dibutyl amine in excess and quantitatively determining the return dibutyl amine with hydrochloric acid).

$CO_2$ Measurement Method:

The $CO_2$ is measured using a gas chromatography technique.

GC Analysis Conditions:

| | |
|---|---|
| Chromatograph | Hewlett-Packard HP5890 No. 6658 05 84 |
| Stainless steel column | PORAPAK T 80–100 Mesh; L: 3 m; ID: 2 mm |
| Oven temperature | 50° C. isothermal |
| Carrier gas | Helium |
| Column flow rate | 46.7 ml/min at 50° C. for P = 243.7 kPa (Fp meter) column + reference: 66.7) |
| Injection | into a glass stripping U-tube |
| Detector temperature | 230° C. |
| Detector | low-sensitivity (range 0) catharometer |
| Volume injected | 0.5 ml of liquid specimen injected into the glass stripping tube |
| Calibration | external calibration by injections of variable volumes of pure $CO_2$. The small volumes (less than 0.1 ml) are obtained by a dilution of 1 ml of $CO_2$/227 ml of helium. |

The method of quantitative determination of hydrolyzable chlorine is carried out according to the AFNOR NF T 52-135 standard.

EXAMPLE 1

800 g of IPDI are charged into a 1-liter reactor and stirred under a stream of argon. The catalyst is introduced in the proportions indicated below at room temperature. The stirring is maintained and the reaction mixture is taken to the reaction temperature, generally 68° C. The evolution of the reaction is monitored by titration of the residual NCO functional groups. Choline, TMBA, i.e. trimethylbenzylammonium, TBA, i.e. tetrabutylammonium, TBP (tetrabutylphosphonium), TOMA (trioctylmethylammonium), trimethylphenylammonium (TMPA) and TOEP (trioctylmethylphosphonium) are tested in the form of hydroxides under the operating conditions below: temperature 68° C. The other operating conditions, the amounts of catalysts and the results are given in the following table.

| Catalyst | Solvent (wt % cata) | [catalyst] wt % | DOC (IPDI) % | Raw MR color value (Hazen) |
|---|---|---|---|---|
| Choline, OH (C)* | Water (50%) | 0.05 | 30 | 159 |
| TMBA, OH (C)* | Water/MeOH (18%) | 0.12 | 34 | 84 |
| TBA, OH | Water (26%) | 0.35 | 48 | 52 |
| TBA, OH | MeOH (26%) | 0.03 | 29 | 47 |
| TBP, OH | Water (50%) | 0.35 | 21 | 35 |
| TMPA, OH (C)* | Water (24%) | 0.35 | 3 | <5 |
| TOMA OH (C)* | Water (50%) | 0.35 | 24 | 228 |
| TMHA, OH | MeOH (50%) | 0.35 | 20 | 35 |
| TOEP, OH (C)* | MeOH (26%) | 0.35 | 9 | 60 |

*(C) = comparative

This table shows that choline gives good yields but a mediocre color value, that TMBA also gives a mediocre color value, TMPA gives an extremely low yield, the aliquot gives a correct yield but a very high color value.

EXAMPLE 2

Role of Catalyst Poisoning

Tests, under the previous conditions with redistilled IPDI, are carried out with as catalyst tetrabutylammonium in hydroxide form dissolved in water at the rate of 26%. The amount of catalyst (dry) used is 0.2%, and 0.4% in the case of the catalyst choline bic, and the reaction temperature is 68° C. The tests are given in the following table.

| Test | DOC (IPDI) % | MR color value (Hazen) |
|---|---|---|
| 120° C. blocking (C)* | — | Yellow (BB)*** |
| DBP blocking ***** | 44 | 9 (BB) *** |
| PTSA blocking ** | 50 | 6 (BB) *** |
|  | 49 | <5 (AB) **** |
| DBP blocking | 51 | 8 (BB) *** |
|  | 50 | <5 (AB) **** |
| Cata choline bic/water | 25 | 46 (BB) *** |
| DBP blocking | 25 | 48 (AB) **** |

* (C) = comparative
** PTSA = paratoluenesulfonic acid
*** (BB) = before blocking
**** (AB) = after blocking
***** (DBP) = dibutyl phosphate.

During the various tests carried out, the procedure consists, when the desired DOC(IPDI) is reached, in adding the DBP directly into the reaction mixture, with stirring, at the reaction temperature. After 30 minutes of treatment, a new sample is taken with titration of the free NCO functional groups and measurement of the color value.

The amount of DBP corresponds to 1 molar equivalent with respect to the initial amount of catalyst introduced. In the case of the catalyst TBA, OH/water, 0.17% of DBP, by weight with respect to the initial IPDI, is then introduced. In the case of the catalyst choline, bic/water, 0.05% by weight is introduced.

In all cases, with choline and TBA catalysts, DBP blocking appears effective, confirms stoppage of the reaction occurring 30 minutes after contact.

EXAMPLE 3

Reactants
(Expressed as a % on a Weight/weight Basis):
IPDI=504 g; the starting $CO_2$ content is measured to be 45 mg/kg of IPDI; the IPDI is distilled before use;
tetrabutylammonium hydroxide (TBA OH) catalyst, 6% TBA OH/2-ethylhexanol-butanol-water (in a mass ratio of 83:12:5) catalyst solution=1.47 g;
blocking solution: 8% PTSA (p-toluenesulfonic acid)/ethylene glycol diethyl ether=1.06 g.
Operating Method
The reaction is carried out in a 1-liter reactor with mechanical stirring, temperature control and argon bubbling via an immersed rod.
After introduction into the reactor, the IPDI is heated for 1 h at 68° C., with stirring, 39 mbar partial vacuum and argon bubbling. The $CO_2$ content is then determined by the method described above to be less than 2 mg/kg of IPDI.
The catalyst solution is introduced over 26 minutes. The reaction mixture is maintained at a temperature of 68° C., with stirring. The progress of the reaction is monitored by titration of the residual isocyanate functional groups. After a total time of 1 h 15 min, the degree of conversion of IPDI reaches 41%, the blocking solution is introduced and, 15 minutes afterwards, the reaction mass is cooled to room temperature. The Hazen color value of the reaction mass is measured to be 12 Hazen.

The reaction mass is distilled over a thin-film evaporator at a temperature of 191° C. and with a vacuum of less than 0.3 mbar.

The final product formulated to a 70% solids content in n-butyl acetate is clear in appearance and has a Hazen color value of 40 Hazen, an NCO content of 12.5% and a viscosity of 342 mPa.s.

EXAMPLE 4

Reactants
(Expressed as a % on a Weight/weight Basis):
IPDI=504 g, the starting $CO_2$ content is measured to be less than 2 mg/kg of IPDI, and the IPDI is distilled before use;
catalyst: tetrabutylammonium hydroxide (TBA OH), 6% TBA OH/2-ethylhexanol-butanol-water (in an 83:12:5) mass ratio) catalyst solution=1.71 g;
blocking solution: 10% PTSA/2-ethylhexanol=0.76 g.
Operating Method
The reaction is carried out in a 1-liter reactor with mechanical stirring, temperature control and argon bubbling via an immersed rod.
After introduction of the IPDI into the reactor, it is maintained for 1 h at 25° C., with stirring and argon bubbling.
The catalyst solution is introduced over 20 minutes. The reaction mixture is heated to a temperature of 50° C., with stirring. The progress of the reaction is monitored by titration of the residual isocyanate functional groups. After a total time of 3 h 7 min, the degree of conversion of IPDI reaches 47%, the blocking solution is introduced and, 15 minutes afterwards, the reaction mass is cooled to room temperature. The Hazen color value of the reaction mass is measured to be 8 Hazen.

The reaction mass is distilled over a thin-film evaporator at a temperature of 191° C. and with a vacuum of less than 0.3 mbar.

The final product formulated to a 70% solids content in n-butyl acetate is clear in appearance and has a Hazen color value of 13 Hazen, an NCO content of 12.5% and a viscosity of 885 Mpa.s.

EXAMPLE 5 COMPARATIVE

Reactants
(Expressed as a % on a Weight/weight Basis):
IPDI=35 g;
catalyst: 2-hydroxyethyltrimethylammonium hydroxide, as a 45% solution in methanol=0.032 g.
Operating Method
The reaction is carried out in a 0.1-liter reactor with mechanical stirring, temperature control and $CO_2$ bubbling via an immersed rod under the same conditions as example 3.
The reaction is carried out at 80° C. and, after a time of 1 h 30 min, the degree of conversion of IPDI reaches 35%. The reaction mass is cooled to room temperature and the Hazen color value is measured to be 191 Hazen.

What is claimed is:

1. Process for cyclotrimerizing isocyanate functional groups by the action of a quaternary-ammonium- or quaternary-phosphonium-based catalyst, characterized in that said isocyanate functional groups are branched and in that said oniums are chosen from those of which the sum of the carbons is at most equal to 30 and at least equal to 12; of which the counterion is chosen from anions corresponding to weak acids whose $pK_A$ is at least equal to 8, preferably 10 and more preferably 12; of which the substituents are aliphatic and do not possess unsaturation in the beta position; and in that said oniums comprise at most 2 radicals of more than 6, advantageously more than 10 and preferably more than 12 carbon atoms.

2. Process for preparing polyisocyanates by (cyclo) trimerizing isocyanate functional groups carried by isocyanates having a branched hydrocarbon backbone, characterized in that it comprises the following steps:
   a) supplying of starting isocyanate monomers;
   b) removal of the reactive gases from said isocyanate monomers;
   c) optionally, supplying of a starting reaction mixture comprising said starting isocyanate monomers;
   d) addition of a (cyclo)trimerization catalyst as defined in claim 1;
   e) reaction until the desired degree of conversion is obtained; and
   f) optionally, removal of the monomers that have not reacted; the order of steps b) and c) not mattering.

3. Process according to claim 1, characterized in that no substituent of said onium carries a hydroxyl functional group.

4. Process according to claim 1, characterized in that said counterion is a hydroxide or an alcoholate or one of the anions which they induce into the reaction mixture.

5. Process according to claim 1, characterized in that the catalyst content of the reaction mixture is between $10^{-5}$ and $10^{-2}$ times the total mass of the isocyanate monomers.

6. Process according to claim 1, characterized in that no substituent of said bnium has fewer than 2, advantageously fewer than 3, carbon atoms.

7. Process according to claim 1, characterized in that all of the substituents of said onium have at least one and at most two radicals of more than 12, advantageously more than 10 and preferably more than 6 carbon atoms.

8. Process according to claim 1, characterized in that the reaction is stopped by the addition of a medium or strong acid chosen from sulfonic acids, advantageously these being oil-soluble; and phosphoric acids, advantageously a monoester or diester of phosphoric acid.

9. Process according to claim 1, characterized in that the isocyanate functional groups are carried by cycloaliphatic isocyanate monomers.

10. Process according to claim 9, characterized in that the isocyanate functional groups are carried by isophorone diisocyanate.

11. Process according to claim 2, characterized in that the reactive gases are removed from the reaction mixture by diffusing in an inert gas.

12. Process according to claim 2, characterized in that the reactive gases are removed by subjecting the reaction mixture to a vacuum of less than $1 \times 10^4$ Pa and then diffusing in an inert gas.

13. Process according to claim 2, characterized in that the $CO_2$ is removed in step b).

14. Process according to claim 2, characterized in that the air dissolved in the liquid or the mass of starting monomers is removed in step b).

15. Composition comprising:
   20 wt % to 80 wt % of compound(s) having isocyanurate rings produced from cycloaliphatic monomer(s);
   $10^{-6}$ to $10^{-2}$ of a quaternary ammonium or phosphonium, the sum of the carbons of which is at most equal to 25 and at least equal to 15 and no substituent of which has fewer than 2, advantageously fewer than 3, carbon atoms;
20% to 80% of cycloaliphatic monomer(s); and having a Hazen color value, relative to the percentage by mass of compound(s) containing isocyanurate rings, of at most 1 Hazen, advantageously at most 0.75 Hazen and preferably at most 0.50 Hazen.

* * * * *